(12) United States Patent
Keppler

(10) Patent No.: US 7,919,486 B2
(45) Date of Patent: Apr. 5, 2011

(54) USE OF GALLIUM(III) COMPLEXES FOR THE TREATMENT OF MELANOMAS

(75) Inventor: Bernhard Keppler, Hockenheim (DE)

(73) Assignee: Niiki Pharma Inc., Hoboken, NJ (US)

( * ) Notice: Subject to any disclaimer, the term of this patent is extended or adjusted under 35 U.S.C. 154(b) by 0 days.

(21) Appl. No.: 12/190,759

(22) Filed: Aug. 13, 2008

(65) Prior Publication Data

US 2009/0137620 A1 May 28, 2009

Related U.S. Application Data

(63) Continuation of application No. PCT/AT2007/000071, filed on Feb. 13, 2007.

(51) Int. Cl.
*A61K 31/555* (2006.01)

(52) U.S. Cl. ........................................ 514/187

(58) Field of Classification Search ............. 514/183, 514/187
See application file for complete search history.

(56) References Cited

U.S. PATENT DOCUMENTS 5,525,598 A 6/1996 Collery et al.

FOREIGN PATENT DOCUMENTS

WO 02/074304 A2 9/2002

OTHER PUBLICATIONS

Valiandi, S.M., et al, Tris (8-quinolinolato) Gallium (III) Exerts Strong Antiproliferative Effects in Melanoma Cells, Metal Ions in Biology and Medicine, vol. 9, pp. 282-286 (2003).*

* cited by examiner

*Primary Examiner* — James D Anderson
(74) *Attorney, Agent, or Firm* — Jun He Law Offices P.C.; James Zhu

(57) ABSTRACT

The invention relates to the use of gallium (III) complexes for the treatment of melanomas.

6 Claims, No Drawings

USE OF GALLIUM(III) COMPLEXES FOR THE TREATMENT OF MELANOMAS

CROSS REFERENCE TO RELATED APPLICATIONS

This application is a continuation of International PCT Application No. PCT/AT2007/000071, designating the United States and filed Feb. 13, 2007, which claims priority to Austrian Patent Application No. 220/2006, filed Feb. 13, 2006, both of which are incorporated herein by reference.

BACKGROUND

The present invention relates to the use of gallium(III) complexes for the treatment of melanomas.

It is known that simple gallium salts, such as gallium(III) chloride and gallium nitrate, are used for fighting tumor diseases in humans. Collery, for instance, describes the use of gallium chloride in the treatment of various human tumors in U.S. Pat. No. 4,596,710. U.S. Pat. No. 4,529,593 describes the use of gallium nitrate, among others, for treating tumor-associated hypercalcemia. A serious drawback of these small inorganic compounds is, on the one hand, the very limited bioavailability in case of an oral application and, on the other hand, the serious nephrotoxicity, which makes a clinical application in humans very difficult (Krakoff et al., Cancer 44, 1722-1727, 1997; Senderowicz et al., Urol. Int. 1999, 63, 120-125; Fagbemi et al. Seminars in Urologic Oncology, 1998, 16, 23-29; Schwartz et al. Anticancer Res. 1984, 4, 317-318). Apart from this, weight loss, pneumonia and liver damage have also been observed in the use of simple gallium salts (Hart et al., J. Natl. Cancer Inst. 47, 1121-1127, 1971). There has therefore been a search for alternatives to the simple gallium salts gallium chloride and gallium nitrate.

A compound that avoids the above-mentioned drawbacks is gallium maltolate, which is being clinically tested at the moment (Lawrence Bernstein, WO 93/09776). This compound is distinguished by a significantly enhanced bioavailability.

Likewise, gallium(III) complexes with nitrogen-containing ligands show a much higher lipophilicity and improved bioavailability upon oral application and could show their anti-tumor effect in experimental animal tumors, such as soft-tissue sarcomas (Collery et al. WO 93/02087; Thiel et al. in: Relevance of Tumour Models for Anticancer Drug Development. Contrib. Oncol. Basel, Karger, 54, 439-442, 1999). Oral application is particularly desired in the case of gallium compounds in the treatment of tumor diseases because due to the mechanism ribonucleotide reductase inhibition these compounds should be administered, if possible, continuously over a long period of time.

WO 02/074304 describes the use of gallium(III) complexes with nitrogen-containing ligands in combination with other therapeutically effective cytostatic agents, such as e.g. various platinum(III) complexes.

DETAILED DESCRIPTION

Surprisingly, it has now been found that gallium(III) complexes of the general formula (I) are particularly useful, also without being combined with other cytotoxic compounds, in the treatment of melanomas. There is a continued great demand for efficient drugs for this indication. It could be shown in preclinical studies that gallium complexes of the general formula (I) exhibit a high activity in the treatment of these cancer diseases.

It is therefore the object of the present invention to treat melanomas.

This object is achieved by the use of a compound of the general formula (I)

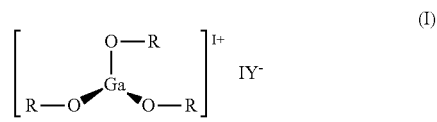

wherein R
is an N-containing group, selected from a group of the general formula (II) to (VII):

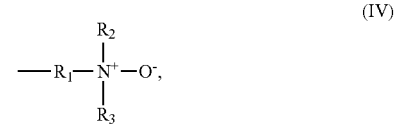

wherein
R$_1$ is C$_1$-C$_6$-alkylene, C$_3$-C$_8$-cycloalkylene, C$_3$-C$_8$-cycloalkenylene, C$_2$-C$_6$-alkenylene, a mononuclear or polynuclear, optionally aromatic, C$_6$-C$_{14}$ ring system or a heterocycle, which may each be substituted or unsubstituted;

R$_2$ and R$_3$ are C$_1$-C$_{10}$-alkyl, C$_3$-C$_8$-cycloalkyl, C$_3$-C$_8$-cycloalkenyl, C$_2$-C$_{10}$-alkenyl, a mononuclear or polynuclear, optionally aromatic, C$_6$-C$_{14}$ ring system or a heterocycle, which may each be substituted or unsubstituted, or hydrogen;

and R$_1$ and R$_2$, or R$_1$ and R$_3$, or R$_2$ and R$_3$ may form a heterocycle which may optionally contain further nitrogen atoms;

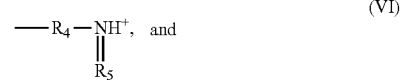

wherein
R$_4$ has the same meaning as R$_1$, R$_5$ has the same meaning as R$_2$, and
R$_4$ and R$_5$ together with N may form an optionally aromatic ring system which may contain further nitrogen atoms;
i is an integer of 0 to 3 and corresponds to the sum of the N-containing groups of formulae (III) and/or (VI);

Y is a halogen, a pseudohalogen, HCO₃ or R'COO, wherein R' is $C_1$-$C_6$-alkyl, $C_2$-$C_6$-alkenyl, $C_3$-$C_6$-cycloalkyl, $C_3$-$C_6$-cycloalkenyl, aryl, which may each be substituted or unsubstituted, and/or a physiologically compatible anion; and physiologically compatible addition salts thereof.

Furthermore, it is preferred that the heterocycle for R1 is a mononuclear or polynuclear basic heterocycle with one or more nitrogen atoms.

In a preferred embodiment, R1 is C1-C6-alkylene, C3-C6-cycloalkylene, C3-C6-cycloalkenylene, C2-C6-alkenylene, C6-C14-arylene or a heterocycle, which may each be substituted or unsubstituted, and $R_2$ and $R_3$ are $C_1$-$C_{10}$-alkyl, $C_3$-$C_6$-cycloalkyl, $C_3$-$C_6$-cycloalkenyl, $C_2$-$C_{10}$-alkenyl, $C_6$-$C_{14}$-aryl or a heterocycle, which may each be substituted or unsubstituted, or hydrogen.

$R_1$ is preferably:
- $C_1$-$C_5$-alkylene, such as n-butylene or n-pentylene, particularly $C_1$-$C_3$-alkylene, such as methylene, ethylene, n-propylene or i-propylene; $C_2$-$C_5$-alkenylene, such as butenylene or pentenylene, particularly $C_2$-$C_3$-alkenylene, such as ethenylene or propenylene;
- $C_3$-$C_6$-cycloalkylene, such as cyclopentylene or cyclohexylene, particularly $C_3$-$C_4$-cycloalkylene, such as cyclopropylene or cyclobutylene; $C_3$-$C_6$-cycloalkenylene, particularly $C_5$-$C_6$-cycloalkenylene, such as cyclopentenylene or cyclohexenylene; $C_6$-$C_{10}$-arylene, particularly benzylene.

$R_2$ and $R_3$ are preferably:
- $C_1$-$C_6$-alkyl, such as n-butyl, n-pentyl, or n-hexyl, particularly $C_1$-$C_3$-alkyl, such as methyl, ethyl, n-propyl or i-propyl;
- $C_2$-$C_6$-alkenyl, such as butenyl, pentenyl, particularly $C_2$-$C_3$-alkenyl, such as ethenyl or propenyl;
- $C_3$-$C_6$-cycloalkyl, such as cyclopentyl or cyclohexyl, particularly $C_3$-$C_6$-cycloalkyl, such as cyclopropyl or cyclobutyl;
- $C_3$-$C_6$-cycloalkenyl, particularly $C_5$-$C_6$-cycloalkenyl, such as cyclopentenyl or cyclohexenyl;
- $C_6$-$C_{10}$-aryl, particularly benzyl.

In a preferred embodiment R4 and R5 form an aromatic ring.

In preferred embodiments R1, R2 and/or R3 are substituted by: hydroxyl, amino, —SO₃H, halogen, $C_1$-$C_4$-alkyl, $C_2$-$C_4$-alkenyl, $C_3$-$C_6$-cycloalkyl, $C_3$-$C_6$-cycloalkenyl, $C_1$-$C_4$-alkoxy, $C_1$-$C_4$-alkoxy-$C_1$-$C_4$-alkylene, $C_1$-$C_4$-alkylmercapto, $C_1$-$C_4$-alkylmercapto-$C_1$-$C_4$-alkylene, formyl, $C_1$-$C_4$-alkoxycarbonyl, $C_1$-$C_4$-alkoxycarbonyl-$C_1$-$C_4$-alkylene, di-$C_1$-$C_4$-alkylamino, di-$C_1$-$C_4$-alkylamino-$C_1$-$C_4$-alkylene, di-$C_1$-$C_4$-alkylaminocarbonyl, di-$C_1$-$C_4$-alkylaminocarbonyl-$C_1$-$C_4$-alkylene.

Furthermore, groups of the general formula (II) are preferably selected from groups of formulae (VIII) and (IX)

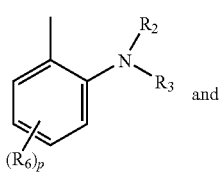
(VIII)

and

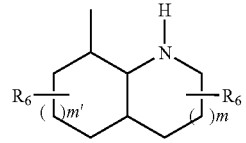
(IX)

wherein $R_2$, $R_3$ are as defined above, $R_6$ is alkyl, cycloalkyl, aryl or heteroaryl, which may each be substituted or unsubstituted, p is 0 to 4, m, m' are 0 to 2, particularly 1.

Furthermore, if p equals 2, two ortho-position substituents R6 may form an optionally aromatic cycle.

In preferred embodiments R6 is substituted, as defined above, for R1, R2 and/or R3.

Groups of the general formula (III) are preferably selected from groups of formulae (X) and (XI)

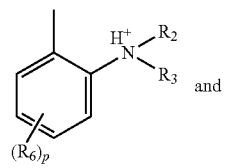
(X)

and

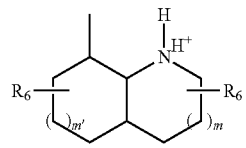
(XI)

wherein $R_2$, $R_3$, $R_6$, p, m, m' are as defined above.

Groups of the general formula (IV) are preferably selected from groups of formulae (XII) and (XII)

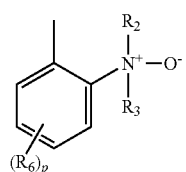
(XII)

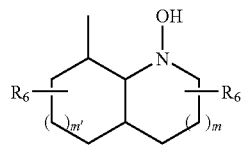
(XIII)

wherein $R_2$, $R_3$, $R_6$, p, m, m' are as defined above.

Groups of the general formula (V) are preferably selected from formulae (XIV) and (XV)

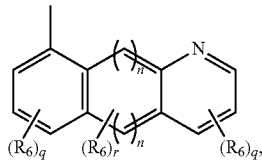
(XIV)

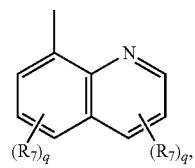
(XV)

wherein
R_6 is as above,
R_7 is alkyl, cycloalkyl, aryl or heteroaryl, which may each be substituted or unsubstituted,
halogen, sulfonyl,
q is 0 to 3,
r is 0 to 2, and
n is 0 to 2, particularly 1.

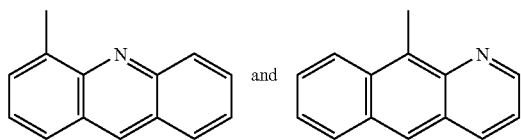

Furthermore, if q or r equals 2, two ortho-position substituents R6 may form an optionally aromatic cycle.

Groups of the general formula (VI) are preferably selected from formulae (XVI) and (XVII)

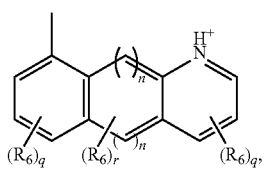
(XVI)

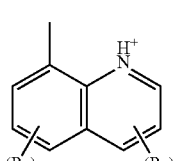
(XVII)

wherein
R_6, R_7, q, r, n are as defined above,

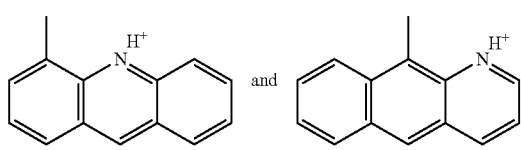

Groups of the general formula (VII) are preferably selected from formulae (XIII) and (XIX)

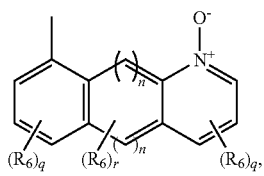
(XVIII)

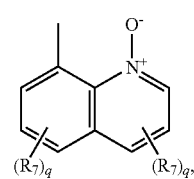
(XIX)

wherein
R_6, R_7, q, r, n
are as defined above,

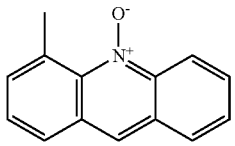 and 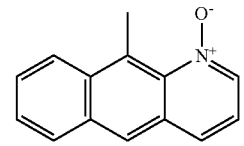

In a further preferred embodiment, Y in the general formula (I) is chlorine.

Particularly preferably, q and r=0 in the groups of formulae (XIV), (XV), (XVI), (XVII), (XVIII) and (XIV).

R in the general formula (I) is quite particularly preferably a group of formula (XV) and (q=0).

The present invention also refers to the use of gallium(III) complexes of the general formula (I) for preparing a medicament for treating melanomas.

The melanomas that are suited for treatment with a gallium complex of the general formula (I) may be an amelanotic melanoma, a lentigo maligna melanoma, an acral lentiginous melanoma, an epitheloid cell melanoma, a nodular melanoma, a melanoma in connection with naevus, a melanoma with superficial spreading or a spindle cell melanoma. Metastases of these tumors in other organs may also be treated with a gallium complex of the general formula (I).

To treat the above-mentioned cancerous diseases, the gallium complex of formula (I) is administered particularly preferably orally, but also intravenously, intramuscularly, intraperitoneally, or subcutaneously. External or local application is also possible. Preferred is an administration by oral application.

The use of gallium(III) complexes according to the invention may be carried out in any suitable formulation, on condition that the formation or maintenance of adequate levels of active ingredients is ensured. This can e.g. be accomplished by way of oral or parenteral administration in suitable doses. Advantageously, the pharmaceutical preparation of the active ingredient is in the form of unit doses that are adapted to the desired administration. A unit dose may e.g. be a tablet, a coated tablet, a capsule, a suppository, or an adequate volume quantity of a powder, granulate, solution, emulsion or suspension.

A "unit dose" within the meaning of the present invention is understood to be a physically defined unit that contains an individual amount of the active ingredient in combination with a pharmaceutical carrier substance, and the active ingredient content of which corresponds to a fraction or multiple of a therapeutic single dose. A single dose preferably contains the amount of active ingredient that is administered in an application and normally corresponds to a whole daily dose, half a daily dose, a third of a daily dose or a quarter of a daily dose. If only a fraction, for instance half of the unit dose or a quarter of the unit dose, is needed for a single therapeutic administration, the unit dose is preferably divisible, e.g. in the form of a tablet with a point of fracture.

If carried out in unit doses and if intended for applications, for example, with humans, the use of gallium(III) complexes according to the invention in a suitable medicament may be performed with about 0.1 mg to 3000 mg, preferably 10 mg to 2000 mg and particularly 30 mg to 1500 mg of active ingredient. The active ingredient may be administered once, but also continuously over a long period of time. With an oral treatment similar dosages may be used.

The therapeutic use of gallium(III) complexes according to the invention in a medicament may take place 1 to 4 times a day at fixed or varying times, e.g. each time before the meals and/or in the evening. However, it may be necessary to deviate from said dosages, namely depending on the type, body weight and age of the individuals to be treated, the kind and severity of the disease, the way of preparation and the application of the medicaments, and the period or interval within which the administration is carried out. For instance, in some cases it may be enough to use less than the above-mentioned amount of active ingredient whereas in other cases the above-indicated amount of active ingredient must be exceeded. It may also turn out to be expedient when the medicament is administered only once or at an interval of several days.

Every person skilled in the art is able to fix the necessary optimal dosage and the type of application of gallium(III) complexes owing to his/her technical knowledge.

The use of gallium(III) complexes according to the invention may be in the form of medicaments that normally comprise the gallium(III) complex and non-toxic pharmaceutically tolerated medicament vehicles that are used as admixture or diluent, e.g. in solid, semisolid or liquid form, or as a coating agent, e.g. in the form of a capsule, a tablet coating, a bag or another container for the therapeutically active ingredient. A carrier substance may e.g. serve as an intermediary for drug uptake by the body, as a formulation excipient, as a sweetener, as a taste corrective, as a dye or as a preservative.

Tablets, coated tablets, hard and soft capsules, e.g. of gelatin, dispersible powder, granulates, aqueous and oily suspensions, emulsions, solutions or syrups, may e.g. be used for oral application.

Tablets may be inert diluents, e.g. calcium carbonate, calcium phosphate, sodium phosphate, or lactose; granulating and distributing agents, e.g. corn starch, polyvinylpyrrolidone, or alginates; binders, e.g. starch, gelatins, or gum arabic; and lubricants, e.g. aluminum or magnesium stearate, talc, or silicone oil. They may additionally be provided with a coating of such a kind that it effects a retarded dissolution and resorption of the medicament preparation in the gastrointestinal tract, resulting e.g. in improved tolerance, protraction or retardation. Gelatin capsules may contain the medicament mixed with a solid diluent, e.g. calcium carbonate or kaolin, or an oily diluent, e.g. olive, peanut or paraffin oil.

Aqueous suspensions may contain suspending agents, such as sodium carboxymethyl cellulose, methyl cellulose, hydroxypropyl cellulose, sodium alginate, polyvinylpyrrolidone, gum tragacanth or gum arabic; dispersing and wetting agents, e.g. polyoxyethylenestearate, heptadecaethyleneoxycatanol, polyoxyethylenesorbitol monooleate, or lecithin; preservatives, such as methyl- or propylhydroxybenzoates; flavoring agents, sweeteners, e.g. saccharose, lactose, sodium cyclamate, dextrose, inverted sugar syrup.

Oily suspensions may contain, for example, peanut, olive, sesame, coconut or paraffin oil and thickening agents, such as beeswax, hard paraffin or cetyl alcohol; furthermore, sweeteners, flavoring agents, and antioxidants.

When gallium(III) complexes are used according to the invention, water-dispersible powders and granulates may for example contain dispersing, wetting and suspending agents, e.g. the above-mentioned ones, as well as sweeteners, flavoring agents and dyes in a mixed state.

Emulsions may e.g. contain olive, peanut or paraffin oil in addition to emulsifying agents, such as e.g. gum arabic, gum tragacanth, phosphatides, sorbitane monooleate, polyoxyethylene-sorbitane-monooleate, as well as sweeteners and flavoring agents.

Aqueous solutions may contain preservatives, e.g. methyl- or propylhydroxybenzoates; thickening agents; flavoring agents; sweeteners, e.g. saccharose, lactose, sodium cyclamate, dextrose, inverted sugar syrup, as well as flavoring agents and dyes.

Sterilely injectable aqueous solutions, isotonic salt solutions, or other solutions, serve the parenteral application of the medicaments.

The invention shall now be explained hereinafter with reference to examples.

EXAMPLES

The compound of tris(hydroxyquinolinolato)gallium(III) was analyzed with respect to its cytotoxic activity in the cell culture on the melanoma cell lines obtained from human tumors.

The compound showed a high activity in the μmolar range:
SK-MEL-5 0.76
SK-MEL-28 35

The invention claimed is:

1. A method of treating melanoma comprising administering to a patient in need of treatment of melanoma an effective amount of a compound of the general formula (I)

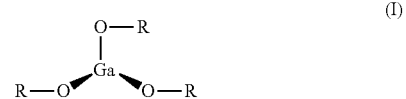

wherein each R is

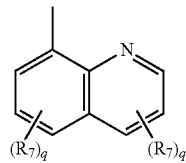

where $R_7$ is alkyl, cycloalkyl, aryl or heteroaryl each of which may be substituted or unsubstituted, or halogen or sulfonyl, and q is an integer of 0 to 3.

2. The method of claim 1, wherein q equals 0.

3. A method of treating melanoma comprising administering to a patient diagnosed of melanoma an effective amount of tris(hydroxyquinolinolato)gallium(III) or a pharmaceutically compatible salt thereof.

4. The method of claim 3, wherein said patient is diagnosed of metastatic melanoma.

5. A method of treating melanoma comprising:
identifying a patient having melanoma, and
administering to said patient an effective amount of tris (hydroxyquinolinolato)gallium(III) or a pharmaceutically compatible salt thereof.

6. The method of claim 5, wherein said patient is diagnosed of metastatic melanoma.

* * * * *